United States Patent [19]

Kato

[11] 4,322,495
[45] Mar. 30, 1982

[54] IMMUNOASSAY

[75] Inventor: Kenneth H. Kato, Cottage Grove, Minn.

[73] Assignee: Minnesota Mining and Manufacturing Co., Saint Paul, Minn.

[21] Appl. No.: 129,357

[22] Filed: Mar. 11, 1980

[51] Int. Cl.$^3$ ............................................. G01N 33/54
[52] U.S. Cl. ........................................ 435/7; 435/810; 23/230 B; 424/12
[58] Field of Search .................. 435/7, 174, 176, 177, 435/317, 810; 424/8, 12, 88; 23/230 B; 260/112 R, 121

[56] References Cited

U.S. PATENT DOCUMENTS 3,654,090  4/1972  Schuurs et al. .......................... 435/7
3,839,153  10/1974  Schuurs et al. .......................... 435/7

OTHER PUBLICATIONS

Wong, "Fate and Immunogenicity of Irradiated Infective Larvae of *Dirofilaria immitis* in the Dog", *Proceedings of the Heartworm Symposium*, Mar. 16–17, 1974, pp. 75–81.

Engvall et al., "Enzyme–Linked Immunosorbent Assay, ELISA", *J. Immunol.*, vol. 109, No. 1, (1972), pp. 129–135.

Wong et al., "Filarial Antibodies and Eosinophilia in Human Subjects in an Endemic Area", *Trans. Roy. Soc. Trop. Med. & Hygiene*, vol. 63, No. 6, (1969), pp. 796–800.

Zam, "Isolation and Characterization of Somatic and Metabolic Antigens and Moulting Fluid Antigens of *Dirofilaria immitus* Adults, Microfilaria, Late First Stage (Sausage-form) and Third Stage Larvae", Gov't Document ADA 044729, (1976).

Wong et al., "Indirect Fluorescent Antibody Test in Occult Dirofilariasis", *Am. J. Vet. Res.*, vol. 40, No. 3, (1979), pp. 414–420.

Qualls et al., "A Rapid Batch Method for the Production of Specific Fluorescein Isothiocyanate-Labeled Globulins to *Dirofilaria immitis* Microfilaria", *Am. J. Vet. Res.*, vol. 36, No. 2, (1975), pp. 235–236.

Welch et al., "Antibodies to *Dirofilaria immitis* in Caucasian and Aboriginal Australians diagnosed by Immunofluorescence and Passive Adults Hypersensitivity", *Chem. Abstracts*, vol. 82, No. 11, p. 311 (1975), Abs. No. 7138g.

Sullivan et al., "Specific Killing of Parasites by Antibody–Enzyme Conjugates", *Chem. Absts.*, vol. 79, No. 21, p. 258, (1973), Abs. No. 124533b.

Voller et al., "Enzyme Immunoassays in Diagnostic Medicine", *Bull. World Health Organ.*, vol. 53, (1976), pp. 55–64.

*Primary Examiner*—Thomas Wiseman
*Attorney, Agent, or Firm*—Cruzan Alexander; Donald M. Sell; Donald C. Gipple

[57] ABSTRACT

An immunoassay for the detection of antibodies for canine heartworm (*D. immitis*) in the blood serum of dogs by immobilizing *D. immitis* microfilariae on a solid support which is then inoculated with a sample of the blood serum being tested, incubated and washed to remove unreacted material then developed utilizing an enzyme-labeled indicating anti-antibody reagent and a substrate therefor. Also disclosed is a related method for detecting canine heartworm microfilariae in canine blood.

24 Claims, No Drawings

IMMUNOASSAY

This invention relates to immunoassays for detecting antibodies for *D. immitis* (canine heartworm) in the blood serum of dogs and *D. immitis* microfilariae in the blood of dogs utilizing whole *D. immitis* microfilariae as an antigenic reagent and developing an observable endpoint through an enzyme-linked anti-antibody.

Canine heartworm disease, caused by *Dirofilaria immitis* (*D. immitis*), occurs commonly all over the world, including the United States. Dogs infected with this worm ordinarily lose physical vigor and become unsuitable for functions that involve vigorous physical exercise. The disease is ultimately fatal.

M. M. Wong et al, J. Am. Vet. Med. Assoc. 163 #2, 133–139 (1973), have described the disease as follows:

"Natural infection is acquired by the introduction of the infective, third-stage larvae into the dog, through a mosquito vector. In about 3 months, the infective larvae, which have developed into the 5th and final stage (young adults between 2 and 3 cm. long), generally reach the heart. In the next 3 months, these young adult worms grow rapidly into full-length (10 to 18 cm.) mature worms and are found usually in the right ventricle and pulmonary artery. Gravid females then begin producing embryonic progenes, called microfilariae, which are usually found in the peripheral circulation. Microfilariae do not grow or develop in the dog, although they are reported to live in the dog for as long as 2 years. When a suitable vector mosquito acquires the microfilariae by taking a blood meal from the infected dog, microfilariae grow into infective larvae in the malpighian tubules of the mosquito in about 10 to 14 days. At this stage, the larvae migrate into the labrum of the mosquito and are capable of entering the dog host through the hole of the mosquito bite when it takes another blood meal."

Antibody to microfilariae cannot be detected in the sera of dogs with the active form of the disease (in which the microfilariae are circulating in the blood) since the microfilariae act as antigenic "sinks" to remove specific antibodies from the circulation of the infected dogs. Thus in dogs with circulating microfilariae the only positive blood test for the detection of canine heart disease would involve the detection of the presence of the microfilariae.

In a minor proportion (perhaps 10–20 percent) of the cases of canine heartworm disease a so-called occult stage occurs (often following an overt stage). Although adult worms are present in the heart during this stage, microfilariae are not demonstrable in the circulation. In such cases, however, the dogs are capable of mounting an immune response to the microfilariae as evidenced by the presence of specific antibody. Wong, M. M., 1974, Southeast Asian J. Trop. Med. Pub. Hlth. 5:480–486.

Dependable and easily available assays for the occult and overt stages of this serious disease (which is widespread throughout the general canine population) are badly needed but have not been discovered heretofore, despite work on the part of various investigators using differing immunological approaches.

Thus, attempts have been made to utilize the enzyme-linked immunosorbant assay (ELISA) method (described by Engvall et al in the Journal of Immunology 109:129–135, 1972, and in U.S. Pat. No. 3,654,090, Schuurs et al, 1972) and various fluorescent antibody tests; see for example Government Document ADA 044729 (Zam, Steven G., *Isolation and Characterization of Somatic and Metabolic Antigens and Moulting Fluid Antigens of Dirofilaria immitis Adults, Microfilaria, Late First Stage (Sausage-form) and Third Stage Larvae*, Department of Zoology, University of Florida, Gainsville, Fla. 32611. Supported by U.S. Army Medical Research and Development Command, Washington, D.C. 20314. March 1976) and Wong et al, Transactions of the Royal Society of Tropical Medicine and Hygiene, 63, No. 6, 796–800 (1969).

The ELISA and, ordinarily, the fluorescent antibody assay depend upon the isolation and use of soluble antigens (the latter being referred to in the above-cited Government document as SAFA: soluble antigen fluorescent antibody) and the isolation and immobilization of a suitable antigenic component pose major immunological problems. In fact, the inability to obtain a soluble antienic component which is produced by the host animal in response to the *D. immitis* organism and is found in its body fluid and which will at the same time not cross-react with related organisms via antibody (i.e. where the isolated material is a "common antigen") appears to be the major difficulty in these approaches.

Another method which has been suggested (Wong et al, ibid.) utilizes the entire microfilariae as the antigen and detects the unknown antibody by means of a fluorescing indicating anti-antibody which is assayed optically through a microscope. However, this method requires elaborate and expensive equipment (e.g. a microscope), is time consuming to carry out and requires trained personnel to interpret the results. And, even when this is done, the results are subjective and susceptible to error.

The Present Invention

In its primary aspect, I, the present invention relates to an immunochemical method for detecting the presence or absence of antibodies specific to *D. immitis* in canine blood serum which comprises (1) immobilizing a multiplicity of *D. immitis* microfilariae on a solid support, (2) inoculating the product of (1) with a sample of blood serum to be tested, incubating the combination and washing unreacted material away from the solid support, (3) exposing the product of (2) to an enzyme-labeled indicating anti-antibody which is specific to canine *D. immitis* antibodies, incubating the combination and washing unreacted material away from the solid support, and (4) applying an indicator capable of reacting with the enzyme of (3) to produce a detectable enzyme-substrate reaction, the development of the enzyme-substrate reaction on the solid support indicating the presence of antibodies specific to *D. immitis* in the sample being tested and the lack of development of the enzyme-substrate reaction thereon indicating the absence of the antibodies from the sample.

This method obviates the various uncertainties and complications of the previous methods alluded to above. It requires no difficult-to-prepare reagents and it can be designed, with proper choice of materials, so that technicians who are not skilled immunologists can carry it out quickly and without special equipment. Further-more, the results obtained are accurate and dependable. For example, a solid support (such as glass or a polymeric material) with whole *D. immitis* microfilariae immobilized thereon can be inoculated with blood serum from a dog suspected of having occult canine heartworm disease, incubated and the unreacted material washed away, the remaining surface incubated in contact with an enzyme-labeled indicating anti-antibody which is specific to canine heartworm antibodies (such as alkaline phosphatase-labeled goat anti-canine IgG), washed and an enzyme substrate (e.g. a color indicator such as nitrophenyl phosphate) applied. In this embodiment, a positive reaction from the substrate (the development of a yellow color in the case of p-nitrophenyl phosphate indicating the formation of p-nitrophenol) indicates the presence of antibodies specific to *D. immitis* and hence the occult form of the disease.

The test is ordinarily considered to be qualitative (only a positive or negative determination of the presence or absence of the occult heartworm disease being made) but it can be made quantitative by taking into consideration the dilution of the serum and reading the degree of a color developed (or other indication) quantitatively, e.g. with a spectrophotometer. In the example cited, the degree of the yellow color can be monitored at a wavelength of 400 nanometers.

The complementary indirect method of the invention, II, enables one to determine the presence or absence of *D. immitis* microfilariae in canine blood by (1) immobilizing a multiplicity of *D. immitis* on a solid support,
(2) adding a predetermined limited quantity of antibody for canine *D. immitis* to a sample of canine blood to be tested,
(3) inoculating the product of (1) with the product of (2), incubating the combination and washing unreacted material away from the solid support,
(4) exposing the support of (3) to an enzyme-labeled indicating anti-antibody which is specific to canine *D. immitis*, incubating the combination and washing unreacted material away from the solid support, and
(5) applying an indicator capable of reacting with the enzyme of (4) to produce a detectable enzyme-substrate reaction, the development of the full enzyme-substrate reaction on the solid support compared to a control run (utilizing a blood test sample known to be free of the microfilariae) indicating the absence of *D. immitis* microfilariae in the sample being tested, and the lack of development or the reduced development of the enzyme-substrate reaction thereon compared to a control run indicating the presence of the microfilariae in the sample.

It will be seen that the quantity of the reagent utilized in (2) above is sufficient to provide a clearly detectable enzyme-substrate reaction when there are no microfilariae in the test sample but less than the quantity which can be absorbed by the microfilariae in a test sample which does contain microfilariae (i.e. in the latter case no reagent antibody must remain to react with immobilized microfilariae).

Again, this test is ordinarily run on a qualitative basis (indicating only the presence or absence of the microfilariae in the sample being tested), but (as suggested in the previous paragraphs) it can be made quantitative by measuring the degree of development of the enzyme-substrate reaction. While the determination of the overt stage of the canine heartworm disease heretofore has not been as difficult as the determination of the occult stage (being carried out by a microfilariae filter test), verification and exercise of judgment by the veterinarian to distinguish *D. immitis* from the commensual *Dipetalonema reconditum* have none-the-less been required (but are not required using the present method II).

These complementary methods for determining the occult and overt stages of the canine heartworm disease are both suited to being utilized in connection with diagnostic kits suitable for use, for example, in veterinarians' offices. Such kits constitute additional and distinct aspects of the invention as follows:

III. An immunochemical test kit having component parts adapted to be used together to determine the presence or absence of antibodies specific to *D. immitis* in samples of canine blood serum, the kit comprising the combination of a. a solid support having a multiplicity of *D. immitis* microfilariae immobilized thereon,
b. an enzyme-labeled indicating anti-antibody which is specific to canine *D. immitis* antibodies and
c. an indicator capable of reacting with the enzyme to produce a detectable enzyme-substrate reaction, whereby the treated support a can be inoculated with a sample of blood serum to be tested and the combination incubated and washed to remove unreacted material, then exposed to b and again incubated and washed to remove unreacted material and finally exposed to c; the development of the enzyme-substrate reaction on the solid support indicating the presence of antibodies specific to *D. immitis* in the sample being tested and the lack of development of the enzyme-substrate reaction thereon indicating the absence of the antibodies from the sample.

IV. An immunochemical test kit having component parts adapted to be used together to determine the presence or absence of *D. immitis* microfilariae in samples of canine blood, the kit comprising the combination of a. a solid support having a multiplicity of *D. immitis* microfilariae immobilized thereon,
b. an enzyme-labeled indicating anti-antibody which is specific to canine *D. immitis* antibodies,
c. an indicator capable of reacting with the enzyme to produce a detectable enzyme-substrate reaction and
d. an antibody for canine *D. immitis*, where a pre-determined limited quantity of antibody d can be mixed with a sample of canine blood to be tested, the treated support a inoculated with the mixture and the combination incubated and washed to remove unreacted material, then exposed to b and again incubated and washed to remove unreacted material and finally exposed to c; the development of the full enzyme-substrate reaction on the solid support compared to a control run utilizing a blood test sample known to be free of the microfilariae indicating the absence of *D. immitis* microfilariae in the sample being tested, and the lack of development of the reduced development of the enzyme-substrate reaction thereon compared to a control run indicating the presence of the microfilariae in the sample.

A final aspect of the invention is the article which is the basis for both immunochemical methods I and II, i.e. the solid support with a multiplicity of *D. immitis* microfilariae immobilized thereon, V. The concentration of the microfilariae thereon is at least sufficient to allow for the development of a detectable immunochemical indication of the presence or absence of *D. immitis* antibodies in a sample to which it is exposed. Preferably, for convenient reading of the endpoint of the test with the naked eye, at least about 1,000 microfilariae are immobilized per square centimeter of the solid support (the maximum dimension of the individual microfilariae being about 240-280 microns) and more preferably about 5,000 microfilariae or more are immobilized per square centimeter. However, the tests can be run using a microscope with 100 or even fewer immobilized microfilariae per square centimeter of support.

The solid support can be composed of a variety of materials including ceramics (especially glass) and polymers (for example polystyrene, polyethylene and polypropylene). An aqueous suspension of microfilariae can be placed on the solid support and dried at a moderate temperature (for example 18-24 hours at 25°-35° C. or 1-3 hours at 50°-65° C.). The percentage of the microfilariae in the suspension which becomes immobilized on the support is increased considerably (i.e. from the order of 10-20 percent up to 70-85 percent) by subsequently fixing them. This can be done by heating the solid support gently to fix the protein in contact with the support (e.g. passing it through an open flame two or three times, total fixation time about 2 seconds) or by utilizing a protein immobilization aid appropriate to the surface of the support.

While a color indicating enzyme-substrate system is preferred, nonchromogenic systems can also be used. The enzyme-substrate system of choice is alkaline phosphatase-p-nitrophenyl phosphate (in which the phosphate interacts with the bound enzyme to produce a yellow color through formation of p-nitrophenol). Additional enzyme-substrate systems which are suitable for use in the present process include, among others,

| Enzyme | Substrate |
| --- | --- |
| horseradish peroxidase | 5-aminosalicylic acid and hydrogen peroxide |
|  | or |
|  | diamino benzidine hydrogen peroxide |
| β-galactosidase | o-nitrophenyl-β-galactopyranoside |

The following examples are illustrative of the present invention but are not in any way limiting of the scope thereof.

EXAMPLE 1

Isolating canine heartworm microfilariae from a sample of blood from a beagle with the disease An equal volume, 50 ml., of Hanks' balanced salt solution is added to 50 ml. of heparinized filaremic blood in a 500 ml. Erlenmeyer flask. Approximately 3-4 milliliters of a phytohemagglutinin solution (Miles-Yeda) is added to the suspension in order to cause the red cells therein to aggregate. The mixture is stirred gently and placed in an ice bath for 15 minutes. The aggregated red cells are separated from the fluid (plasma plus microfilariae) by gently pipetting off the fluid into 50 ml. centrifuge tubes. Hanks' balanced salt solution (50 ml.) is added to the aggregated red blood cells to resuspend them, and the mixture is again allowed to settle and the fluid is pipetted off and saved. This procedure is repeated 10 to 15 times, or until microscopic examination of the blood indicates an absence of microfilariae (Wong, M. M., 1964. Amer. J. Trop. Med. 13:66-77).

The supernatants from the preceding procedure are combined and aliquoted into a number of centrifugation tubes which are centrifuged for 15 minutes at 1200 rpm at refrigeration temperatures (approximately 4° C.). The supernatants are then discarded and the pellets containing the concentration of microfilariae and a few remaining blood cells are combined and resuspended gently in 50 ml. of Hanks' balanced salt solution.

The tube is then refrigerated and examined periodically for sedimentation of red cell aggregates (approximately 10-15 minutes). The suspension above the sedimented red cells is pipetted off gently, transferred to a clean 50 ml. tube and centrifuged at 1200 rpm for 15 minutes. The supernatant fluid is discarded, and the pellets again gently resuspended in Hanks' balanced salt solution. Differential sedimentation of red cell aggregates is repeated until the microfilariae suspension is relatively free of red blood cells (2-3 times). The final pellet is resuspended in distilled water to lyse (i.e. burst or disintegrate) the remaining blood cells. The suspension is washed 3-4 times in Hanks' balanced salt solution, and resuspended in approximately 10 ml. of sterile distilled water.

EXAMPLE 2

Preparing the reagent: Enzyme≡Antibody$_2$

Whole goat anti-canine globulin includes IgA, IgD, IgE, IgG and IgM fractions. The IgG fraction or anti-canine IgG (Antibody$_2$ herein) is isolated and prepared by the following procedures:

The globulin fraction is isolated from normal dog serum by adding 33 percent saturated ammonium sulfate to precipitate the globulin fraction, then centrifuged. The precipitated globulin fraction is then incubated with DEAE-Sephadex (Pharmacia Fine Chemicals, Piscataway, N.J.) to remove the globulins other than the IgG. The resulting material is then filtered using a Büchner funnel, and the filtrate (the desired IgG solution) is shown by immunoelectrophoresis to contain only IgG. (Baumstark, J. S., Laffin, R. J. and Bardawil, W. A. 1964, Arch. Biochem. Biophy. 108:514-522.)

Glutaraldehyde (diluted to 2.5 percent, w/w) is added to the canine IgG to a final ratio of 10 milligrams of glutaraldehyde to 100 mg. of canine IgG, resulting in a gel (the IgG is crosslinked by the glutaraldehyde). The insolubilized IgG-gel is crushed repeatedly, forming particles of gel to which the IgG is attached. Affinity chromatography is ultilized to isolate from goat anti-canine globulin only those antibody molecules specific for IgG as follows: The gel is incubated with the anti-canine globulin, washed, and the anti-canine IgG is eluted from the gel using 0.1 m. glycine.HCl buffer, pH 2.8. (Avrameas, S. and Ternynck, 1969, ImmunoChem. 6:53-66). The resulting purified anti-canine IgG is then conjugated to the enzyme (alkaline phosphatase type VIII in 3:2 molar ammonium sulfate, available from the Sigma Chemical Corp., St. Louis, Mo.) using a final glutaraldehyde concentration of 0.2 percent, and an IgG/enzyme protein ratio of 1:3. (Engvall, E. and Perlmann, P., 1972, J. Immunol. 109:129-135.)

The alkaline phosphatase-labeled anti-canine IgG (Enzyme≡Antibocy$_2$) is stabilized with 5 percent human serum albumin and held at 4° C. for use in the process of the invention.

Alternately, rabbit anti-canine IgG (Antibody$_2$) (available from the Colorado Serum Co., Denver, Colo.) and labeled with the same enzyme can also be used in the process of the invention.

EXAMPLE 3

Immobilizing the microfilariae on a solid support

Fifty lambdas (0.050 milliliter) of the microfilarial suspension from Example 1 are pipetted onto a 6×6 mm. glass coverslip supported on a 6×6 mm. glass cylinder in a petri dish and air dried at 65° C., then heated gently (by two or three quick passes over an open flame) to fix the microfilariae to the glass surface. Approximately 3600 microfilariae remain affixed to the coverslip (i.e. a concentration of 10,000 microfilariae per square centimeter). The coverslip with microfilariae is stored in a desiccator at 4° C.

Alternatively, the microfilariae can be immobilized for convenience of later use in the bottom of a 4 ml. glass test tube of which the internal surfaces (other than the bottom) are covered by a low adhesion silicone coating. The test tube is siliconized on its internal surfaces by rinsing it with a silicone solution (one part of a silicone concentrate available under the trade designation "Siliclad" from the Clay Adams division of Becton, Dickinson and Company of Parsippany, N.J. in 100 parts of water) then drying in a 50°–60° C. oven. The silicone is removed from the rounded bottom of the test tube with a concentrated aqueous sodium hydroxide solution with a cotton swab soaked in the sodium hydroxide solution, or, preferably, by pipetting a small amount of the solution into the tube and removing it by vacuum suction through a small tube. In either case, the walls of the tube are not touched. The sodium hydroxide remaining on the bottom of the tube is removed by repeated washings with distilled water.

EXAMPLE 4

Inoculating the product of Example 3 with canine serum samples to be tested

Glass coverslips from Example 3 (with microfilariae immobilized thereon) are bathed for 10 minutes in 0.9 percent sodium chloride containing 9.5 percent of a surfactant (polyoxyethylene [20] sorbitan monolaureate available from the Fisher Scientific Company under the trade designation "Tween 20") and 0.02 percent sodium azide (to prevent bacterial growth).

Each coverslip is supported on a glass cylinder placed at the bottom of a large petri dish lined with moistened filtered paper to prevent drying of serum samples during incubation, and 25 lambdas of the canine serum sample to be tested are placed thereon.

The serum and coverslips are incubated at 37° C. for 30 minutes. The coverslips are then washed 3-4 times with PBS/Tween 20 ® diluent solution, drained and replaced on the cylinder supports.

EXAMPLE 5

Exposing the product of Example 4 to reagent of Example 2, incubating and washing The coverslips are flooded with 25 lambdas of a 1:100 dilution of the reagent from Example 2 above (Enzyme≡Antibody$_2$) in the PBS/Tween 20 diluent solution and incubated at 37° C. for an additional 30 minutes.

(The working titer of the enzyme reagent, 1:100, is determined using polystyrene microtiter plates. Wells of the microtiter plate are coated with canine globulin in alkaline carbonate buffer, 0.1 M, pH 9.8, washed in PBS/Tween 20, and reacted with dilutions of the enzyme reagent. The titer of the reagent, 1:100, is determined following addition of the enzyme substrate, p-nitrophenyl phosphate, and it is confirmed by conducting a checkerboard dilution series using dilutions of known positive and negative canine sera against dilutions of the alkaline phosphatase-labeled anti-canine IgG.)

The coverslips are then washed extensively in solutions of the diluent solution.

EXAMPLE 6

Applying the color indicator (substrate)

Twenty lambdas of the enzyme substrate, p-nitrophenyl phosphate (5 mg/1.2 ml. H$_2$O), together with 20 lambdas of 2-amino-2-methyl-1-propanol (1.5 M/l) are then placed on each coverslip. The reactions are allowed to proceed at room temperature until a yellow color (p-nitrophenol) develops on a coverslip containing a positive control (usually 10 to 15 minutes). The reactions are stopped by the addition of a few drops of 1 N NaOH to each coverslip.

The blood sera from fourteen dogs are included in the tests. Of these, nine (designated A-I) are free of canine heartworm disease, three (designated J-L) have canine heartworm microfilariae circulating in their blood (serum) and two (designated M-N) have occult heartworm disease. The test results are presented in Table I.

TABLE I

| Dog Designation | Circulating Microfilariae | Heartworm Disease | Serum Titer (1) | Occult Heartworm Disease Screen (2) |
|---|---|---|---|---|
| A | — | — | 1:5 | — |
| B | — | — | 1:5 | — |
| C (3) | — | — | 1:5 | — |
| D | — | — | 1:10 | — |
| E | — | — | 1:10 | — |
| F | — | — | 1:10 | — |
| G | — | — | 1:5 | — |
| H | — | — | 1:5 | — |
| I | — | — | 1:20 | — |
| J | + | + | 1:1 | — |
| K | + | + | 1:1 | — |
| L | + | + | 1:10 | — |
| M | — | + | 1:40 | + |
| N | — | + | 1:320 | + |

(1) Based on dilutions of 1:1, 1:5, 1:10 and twofold thereafter.
(2) Based on the Serum Titer at a dilution of 1:30.
(3) The serum of dog C is found to contain an elevated white blood cell cound, indicating a possible undetected infection or disease condition.

EXAMPLE 7

The detection of canine heartworm microfilariae in canine blood

To simulate an overt infection, canine microfilariae are isolated as in Example 1, counted microscopically and stored at 4° C. in phosphate buffered saline, 0.01 M, pH 7.4. A quantity of this suspension representing approximately 20,000 organisms is centrifuged at 1200 rpm for ten minutes in a conical shaped centrifuge tube. The supernatant is discarded and the pellet (of microfilariae) is incubated at 37° C. for 30 minutes with 0.1 ml. of a known microfilariae antibody reagent (comprised of pretested blood serum from a dog with an occult infection titered and approriately diluted). The resulting suspension corresponds to the blood of a dog with active heartworm disease (i.e. whose blood contains *D. immitis* microfilariae) which has been treated with a limited quantity of antibody for canine *D. immitis*. It is centrifuged at 1200 rpm for b 10 minutes, the pellet is discarded and the supernatant serum is tested for the presence of antibody using the enzyme test described in Examples 4-6. The absence of formation of a color (as would be induced by an active enzyme on the substrate) is indicative of the comsumption of the known antibody by the microfilariae.

EXAMPLE 8

Variations in the technique of immobilizing microfilariae on solid supports

Fifty lambdas of an aqueous microfilariae suspension prepared as in Example 1 are pipetted onto a glass coverslip for each of the following lots, A through J, the suspension is dried and fixed to the slide, the coverslip is washed 6 times in phosphate buffer, stained using 1 percent aqueous methylene blue (1 minute exposure) and the microfilariae remaining fixed on the coverslip are counted microscopically in the most concentrated field on the coverslip, which is equivalent to 200×magnification. Variations from lot to lot in the procedures used are as follows:

A. The suspension is air-dried at 55° C. for 1-2 hours, then heated gently by passing the coverslip quickly through an open flame two or three times to fix the protein in contact with the coverslip (total fixation time about 2 seconds).

B. Air-dry as in lot A (no further treatment).

C. The coverslip is soaked in a 0.06 percent solution of the dimethylamine adduct of epoxidized poly-cis-butadiene (DIMA, disclosed in U.S. Pat. No. 4,210,722, which serves as a protein immobilization aid) and dried for 30 minutes at 37° C. The microfilariae suspension is then pipetted onto the thus treated coverslip and airdried as in lot A.

D. The procedure of lot C is repeated except that the coverslip is treated with a different protein immobilization aid (SiTCDI, silane-terminated polycarbodiimide, disclosed in U.S. Pat. No. 4,118,536).

E. The suspension is allowed to settle on the coverslip for 24 hours at 37° C.

F. The coverslip is treated with DIMA as in lot C. The microfilariae suspension is then pipetted onto the thus treated coverslip and allowed to settle for 24 hours at 37° C. as in lot E.

G. The coverslip is treated with SiTCDI as in lot D. The microfilariae suspension is then pipetted onto the thus treated coverslip and allowed to settle for 24 hours at 37° C. as in lot E.

H. One percent of glutaraldehyde is added to the suspension to serve as a protein immobilization aid which is allowed to settle for 1 hour at 37° C.

I. The procedure is the same as in lot H except that 0.1 percent of glutaraldehyde is added to the suspension.

J. The procedure is the same as in lot H except that 0.01 percent of glutaraldehyde is added to the suspension.

The results of lots A-J are shown in the following table.

| Lot | Type of Immobilization Procedure | Percentage of Microfilariae Immobilized* |
|-----|----------------------------------|------------------------------------------|
| A | Air-dry (at 55° C.) and flame fix. | 76 |
| B | Air-dry only. | 19 |
| C | Air-dry only; coverslip treated with DIMA. | 26 |
| D | Air-dry only, coverslip treated with SiTCDI. | 73 |
| E | Settle (at 37° C.) only. | 1 |
| F | Settle only; coverslip treated with DIMA. | 3 |
| G | Settle only; coverslip treated with SiTCDI. | 0 |
| H | 1% glutaraldehyde added to the suspension. | 4 |
| I | 0.1% glutaraldehyde added to the suspension. | 0.1 |
| J | 0.01% glutaraldehyde added to the suspension. | 0 |

*Of the total number originally added to the coverslip.

In another series of lots, 50 lambda of the aqueous microfilariae suspension is pipetted onto a glass or polymeric support. Prior to adding the suspension, the glass supports (coverslips) are soaked in approximately 5 N aqueous sulfuric acid, heated to boiling for 30-60 minutes and rinsed extensively (5-6 times) in deionized water and dried at 150° C. The polymeric supports (4 mil, i.e. approximately 0.1 mm., polystyrene film available from the Dow Chemical Co.) are used without pre-treatment, unless otherwise specifically stated. These suspensions are allowed to dry for 30-60 minutes at 56° C. and are then washed three times with PBS (phosphate-buffered saline). Blood serum is added (to simulate the actual conditions of the test) and the support is washed six times with PBS then subjected to 1 percent aqueous methylene blue for 1 minute, after which it is washed twice with water and dried. The remaining attached microfilariae are then counted as in lots A-J.

Glass supports are used for lots K, L and M and polymeric supports for lots N, O and P. The specific lot to lot variations in procedures used are as follows:

K and N. No additional treatment.

L. The glass coverslip is soaked for 2 hours at room temperature (approximately 25° C.) in a 0.1 percent solution of SiTCDI in toluene. The coverslip is then air-dried at 37° C.

M. The suspension is fixed (after air-drying) by passing it 2 or 3 times over an open flame as in lot A.

O. The polymeric surface is pre-treated with a 0.1 milligram per milliliter solution of poly-L-lysine (30,000–70,000 molecular weight, available from the Sigma Chemical Company) in PBS for 2 hours at room temperature to immobilize the microfilariae. The support is then washed 3 times with PBS.

P. The polymeric surface is pre-treated with a mixture of 50 percent by weight of a 0.1 percent solution of glutaraldehyde and 50 percent by weight of a 0.1 molar carbonate buffer, pH 9.0, for 2 hours at 56° C. The film is then washed 3-5 times in water and air-dried.

The results of these lots are shown in the following table:

| Lot | Support | Type of Immobilization Procedure* | Percentage of Microfilariae Immobilized** |
|-----|---------|-----------------------------------|-------------------------------------------|
| K | Glass | None. | 10 |
| L | Glass | Support treated with SiTCDI. | 79 |
| M | Glass | Flame fix. | 61–74 |
| N | Polymer | None. | 9 |
| O | Polymer | Support treated with poly-L-lysine. | 69 |
| P | Polymer | Support treated with glutaraldehyde. | 82 |

*In addition to air drying.
**Of the total number originally added to the coverslip.

What is claimed is:

1. An immunochemical method for determining the presence of antibodies specific to *D. immitis* in canine blood serum by means of a detectable enzyme-substrate reaction which comprises
   (1) inoculating a multiplicity of intact or whole canine *D. immitis* microfilariae immobilized on a solid surface with a sample of blood serum to be tested;
   (2) incubating the components of (1) to allow the components to react;
   (3) washing to remove unreacted material from the solid surface;
   (4) introducing an enzyme-labeled indicating anti-antibody which is specific to canine *D. immitis* antibodies to the remaining solid surface;
   (5) incubating the components of (4) to allow the components to react;
   (6) washing to remove unreacted material from the solid surface; and
   (7) applying to the solid surface an indicator capable of reacting with the enzyme of (4) to produce a detectable enzyme-substrate reaction.

2. A method according to claim 1 wherein the solid support is ceramic.

3. A method according to claim 2 wherein the solid support is glass.

4. A method according to claim 1 wherein the solid support is polymeric.

5. A method according to claim 4 wherein the solid support is polystyrene.

6. A method according to claim 1 wherein the enzyme-labeled indicating anti-antibody is phosphatase-labeled goat anti-canine IgG and the enzyme substrate is nitrophenyl phosphate.

7. An immunochemical method for determining the presence or absence of *D. immitis* microfilariae in canine blood which comprises
   (1) adding to a sample of canine blood to be tested a predetermined limited quantity of antibody for canine *D. immitis* which will be rendered nonactive by microfilariae in the sample, but which is sufficient to result in a detectable reaction in step (8) hereof if no microfilariae are present in the sample;
   (2) inoculating a multiplicity of intact or whole canine *D. immitis* microfilariae immobilized on a solid surface with the product of (1);
   (3) incubating to allow the components to react;
   (4) washing to remove unreacted material from the solid surface;
   (5) introducing an enzyme-labeled indicating anti-antibody which is specific to canine *D. immitis* antibodies;
   (6) incubating to allow the components to react;
   (7) washing to remove unreacted material from the solid surface; and
   (8) applying to the solid surface an indicator capable of reacting with the enzyme to produce a detectable enzyme-substrate reaction.

8. A method according to claim 2 wherein the solid support is ceramic.

9. A method according to claim 8 wherein the solid support is glass.

10. A method according to claim 2 wherein the solid support is polymeric.

11. A method according to claim 10 wherein the solid support is polystyrene.

12. A method according to claim 2 wherein the enzyme-labeled indicating anti-antibody is phosphatase-labeled goat anti-canine IgG and the enzyme substrate is nitrophenyl phosphate.

13. An immunochemical test kit having component parts adapted to be used together to determine the presence or absence of antibodies specific to *D. immitis* in samples of canine blood serum, the kit comprising the combination of
   a. a solid support having a multiplicity of *D. immitis* microfilariae immobilized thereon,
   b. an enzyme-labeled indicating anti-antibody which is specific to canine *D. immitis* and
   c. an indicator capable of reacting with the enzyme to produce a detectable enzyme-substrate reaction,
whereby the treated support a can be inoculated with a sample of blood serum to be tested and the combination incubated and washed to remove unreacted material, then exposed to be and again incubated and washed to remove unreacted material and finally exposed to c; the development of the enzyme-substrate reaction on the solid support indicating the presence of antibodies specific to *D. immitis* in the sample being tested and the lack of development of the enzyme-substrate reaction thereon indicating the absence of the antibocies from the sample.

14. A test kit according to claim 13 wherein the solid support is ceramic.

15. A test kit according to claim 14 wherein the solid support is glass.

16. A test kit according to claim 13 wherein the solid support is polymeric.

17. A test kit according to claim 16 wherein the solid support is polystyrene.

18. A test kit according to claim 13 wherein the enzyme-labeled indicating anti-antibody is phosphatase-labeled goat anti-canine IgG and the enzyme substrate is nitrophenyl phosphate.

19. An immunochemical test kit having component parts adapted to be used together to determine the presence or absence of *D. immitis* microfilariae in samples of canine blood, the kit comprising the combination of
   a. a solid support having a multiplicity of *D. immitis* microfilariae immobilized thereon,
   b. an enzyme-labeled indicating anti-antibody which is specific to canine *D. immitis* antibodies,
   c. an indicator capable of reacting with the enzyme to produce a detactable enzyme-substrate reaction and
   d. an antibody for canine *D. immitis*,
whereby a pre-determined limited quantity of antibody d can be mixed with a sample of canine blood to be tested, the treated support a inoculated with the mixture and the combination incubated and washed to remove unreacted material, then exposed to b and again incubated and washed to remove unreacted material and finally exposed to c; the development of the full enzyme-substrate reaction on the solid support compared to a control run utilizing a blood test sample known to be free of the microfilariae indicating the absence of *D. immitis* microfilariae in the sample being tested, and the lack of development or the reduced development of the enzyme-substrate reaction thereon compared to a control run indicating the presence of the microfilariae in the sample.

20. A test kit according to claim 19 wherein the solid aupport is ceramic.

21. A test kit according to claim 20 wherein the solid support is glass.

22. A test kit according to claim 19 wherein the solid support is polymeric.

23. A test kit according to claim 22 wherein the solid support is polystyrene.

24. A test kit according to claim 19 wherein the enzyme-labeled indicating anti-antibody is phosphatase-labeled goat anti-canine IgG and the enzyme substrate is nitrophenyl phosphate.

* * * * *

UNITED STATES PATENT AND TRADEMARK OFFICE
CERTIFICATE OF CORRECTION

PATENT NO. : 4,322,495
DATED : March 30, 1982
INVENTOR(S) : Kenneth H. Kato

It is certified that error appears in the above—identified patent and that said Letters Patent is hereby corrected as shown below:

In column 2, line 21, change "antienic" to -- antigenic --.

In column 3, line 38, change "support" to -- product --.

In column 4, line 48, change "where" to -- whereby --.

In column 4, line 59, change "development of the reduced" to -- development or the reduced --.

In column 12, line 32 (claim 13), change "be" to -- b --.

Signed and Sealed this

Thirteenth Day of July 1982

[SEAL]

Attest:

Attesting Officer

GERALD J. MOSSINGHOFF

*Commissioner of Patents and Trademarks*